United States Patent [19]

Berson

[11] 4,246,893

[45] Jan. 27, 1981

[54] INFLATABLE GASTRIC DEVICE FOR TREATING OBESITY

[76] Inventor: Daniel Berson, 199 Kings Highway, Congers, N.Y. 10920

[21] Appl. No.: 922,229

[22] Filed: Jul. 5, 1978

[51] Int. Cl.³ .................. A61B 19/00; A61B 17/00
[52] U.S. Cl. ................................. 128/1 R; 128/346
[58] Field of Search ............... 128/303 R, 311, 341, 128/1 R, 325, DIG. 9

[56] References Cited

U.S. PATENT DOCUMENTS

| | | | |
|---|---|---|---|
| 3,046,988 | 7/1962 | Moreau et al. | 128/328 |
| 3,055,971 | 9/1962 | Kulick | 128/329 |
| 3,467,101 | 9/1969 | Fogarty et al. | 128/341 |
| 3,538,917 | 11/1970 | Selker | 128/326 |
| 3,600,718 | 8/1971 | Boone | 3/36 |
| 3,646,929 | 3/1972 | Bonnar | 128/1 R |
| 3,739,750 | 6/1973 | Shinjo | 128/344 |
| 3,831,583 | 8/1974 | Edmunds et al. | 128/1 R |
| 3,841,304 | 10/1974 | Jones | 128/1 R |
| 3,852,832 | 12/1974 | McGhan et al. | 3/36 |
| 3,863,639 | 2/1975 | Kleaveland | 128/334 R |
| 3,883,902 | 5/1975 | Lynch | 3/36 |
| 3,903,894 | 9/1975 | Rosen et al. | 128/346 |
| 3,919,724 | 11/1975 | Sanders et al. | 3/36 |
| 4,019,499 | 4/1977 | Fitzgerald | 128/1 R |
| 4,095,295 | 6/1978 | Lake | 3/36 |
| 4,102,342 | 7/1978 | Akiyama et al. | 128/325 |
| 4,133,315 | 1/1979 | Berman et al. | 128/344 |

*Primary Examiner*—Robert W. Michell
*Assistant Examiner*—Thomas Wallen
*Attorney, Agent, or Firm*—Kenyon & Kenyon

[57] ABSTRACT

Apparatus for treating extreme obesity comprising means for compressing the stomach and reducing its capacity and procedures employing said apparatus.

1 Claim, 6 Drawing Figures

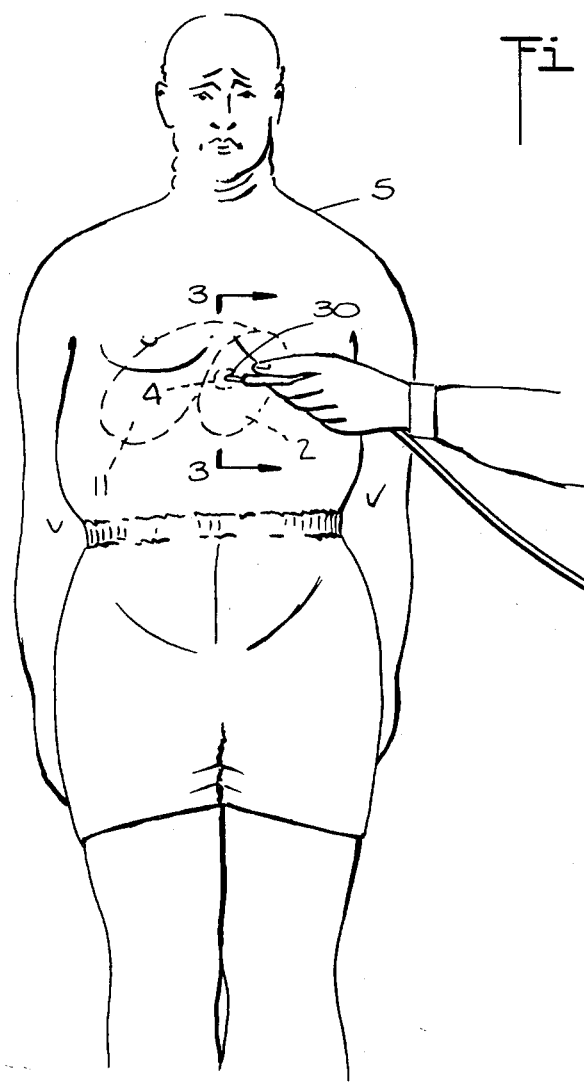
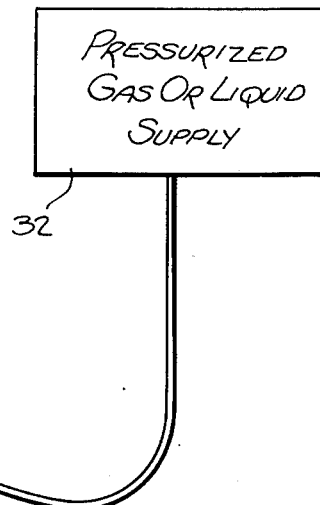
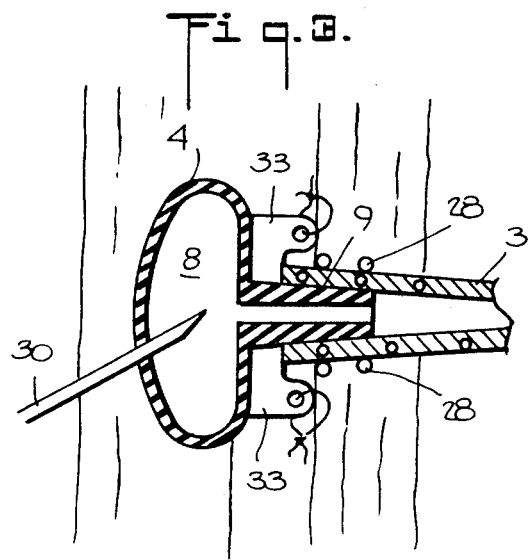
Fig. 1.
Fig. 2.
Fig. 3.
Pressurized Gas Or Liquid Supply

INFLATABLE GASTRIC DEVICE FOR TREATING OBESITY

BACKGROUND OF THE INVENTION

This invention relates to procedures and apparatus for treating obesity in human patients.

In the past, rather drastic surgical procedures have been employed to treat morbidly or mortally obese patients, i.e., patients whose body weight is at least twice their appropriate weight. One set of surgical procedures induces a pathophysiologic abnormality of the gastrointestinal tract by gastric or jejunoileal bypass operations in which as much as 95% of the tract is surgically bypassed. These procedures result in a patient who is a metabolic cripple having surgically induced malabsorption, and are associated with long term complications often requiring additional surgical procedures. The jejunoileal bypass, for example, has been used extensively in this country and around the world. This procedure bypasses about 95% of the small bowel, leaving about 40 cm. of functioning jejunum and ileum. The physiologic effect of this is massive diarrhea and malabsorption of nutrients, leading to weight loss secondary to poor absorption of nutrients, as well as aversion to eating. The procedure is performed an estimated five thousand to twenty thousand times per year in the United States, but has been abandoned by many institutions, including the Cleveland Clinic, because of unacceptable operative mortality averaging 6% nationwide, as well as severe complications including wound infection and breakdown, progressive liver failure, hypocalcemia, calcium oxalate urinary calculi and bypass enteropathy. Mechanical problems such as intestinal obstruction and hernia formation are frequent.

Approximately 32% of the patients having jejunoileal bypass operations are rehospitalized within one year. These operations have also been associated with liver dysfunctions most likely caused by the preferential absorption of carbohydrates in the remaining small bowel, with resulting relative protein starvation.

Because of all these problems, attention has been directed toward gastric surgical procedures to induce weight loss. A gastroplasty procedure was performed by Mason et al. (University of Iowa) to change the shape of the stomach but abandoned because of the technical difficulty of obtaining a proper partial outflow obstruction of the proximal gastric pouch. Instead, these investigators now recommend a 90% gastric bypass in which the proximal 10% of the stomach is anastomosed to the jejunum. This procedure is associated with a 3% operative mortality, as well as frequent would infections, anastomotic breakdowns, and a frequent need to revise the anastomosis. Other approaches to reducing the size of the stomach to cause weight loss include that of Wilkinson (Cited in Alden) who performed a "gastric inversion" with Marlex mesh wrapping in 2 cases, and that of Tretbar, who performed a gastric plication in 20 cases.

Another set of surgical procedures has involved oral surgical techniques to wire shut a patient's jaws to reduce food intake. This involves the serious possibility that any vomiting which may occur can result in aspiration of food and gastric secretions into the lungs.

Non-surgical treatment of obesity by the use of non-nutritive means such as methyl cellulose to fill the stomach is also known. For example, the use of tablets is known which after ingestion together with a fluid swell to a soft, stomach-filling bolus. However, it is appreciated that these means are not usually a satisfactory treatment for patients having the extreme disorder here described.

Mechanical apparatuses are known for insertion through the esophagus into the stomach to conform to the internal shape of the stomach, for example, to fill the stomach and to prevent hemorraging into the stomach from blood vessels at the stomach wall. For example, U.S. Pat. Nos. 3,046,988 and 3,055,371 describe the use of esophago-gastric balloons for such purposes. However, these apparatuses, when utilized, would obstruct the esophagus and, by filling the stomach, interfere with all ingestion of food.

Incontinence devices are also known which may be non-surgically inserted into a patient through an external orifice to entirely seal off passages to an internal organ. For example, U.S. Pat. No. 3,841,304 discloses an inflatable balloon-like bulb for non-surgical partial insertion into the bladder of a female to temporarily seal the entrance from that organ to the urethra so as to restore control over the flow of urine from the bladder. U.S. Pat. No. 3,646,929 discloses a more complex device for vaginal insertion to accomplish control over bladder emission. This device can be made to expand so that a flexible diaphragm displaces the urethra and bladder neck and prevents emptying of the bladder. In both of these cases the control of these devices is accomplished by means of an inflation bulb extending outside the patient's body.

It has been known to place an inflatable apparatus within a patient's abdomen during surgery for use as a retractor to retain the viscera during suturing, for example, as described in U.S. Pat. No. 3,863,639. Such an apparatus, however, is not an implant apparatus, i.e., it is not adapted to remain entirely within the patient postoperatively, and plays no direct role in the control of any disorder.

Accordingly, an object of the invention is to treat mortally or morbidly obese patents without including malabsorption of nutrients in the gastrointestinal tract.

Another object of the present invention is to avoid the complications associated with bypass operations on the gastrointestinal tract.

A further object of the invention is to treat mortally or morbidly obese patients whereby the patient's stomach may be compressed to a controlled degree and adjustments made from time to time in the amount of compression by outpatient treatment.

A still further object of the invention is to provide a relatively simple procedure for treating mortally or morbidly obese patients whereby a feeling of satiety from hunger and a reduction in the capacity of the stomach is produced without intrusion into the gastrointestinal tract.

A still further object of the invention is to provide a surgical implant apparatus that is simple to manufacture for the control of morbid obesity in patients.

These and other objects of the invention will appear more fully in the following specification taken with the accompanying drawings.

SUMMARY OF THE INVENTION

Briefly, this invention provides surgical implant apparatus which is useful for treating a condition of extreme obesity and related procedures employing the apparatus for such treatment.

The implant apparatus comprises an adjustable gastric compression means capable of providing substantially constant upper abdominal distension to give a sensation of satiety or fullness and reducing the capacity of the stomach. The gastric compression means includes a distensible means, for example, a balloon of rubber or similar flexible composition, an attached filling tube for inflating the balloon with a fluid or gas and an adjusting port mated to the filling tube for controlling the amount of fluid or gas retained in the balloon.

The procedure for using the implant apparatus involves abdominal surgery, wherein the distensible means is placed adjacent to the stomach and preferably anterior to the stomach, posterior to the left lobe of the liver. During the procedure, the filling tube may be brought out to a suitable subcutaneous location and trimmed to an appropriate length while the adjusting port is then attached and left in a subcutaneous position at completion of the surgery.

When in place entirely within the patient and filled with fluid (which may be either a liquid or gas), the balloon compresses the stomach (or at least prevents the expansion of the stomach into the space that would otherwise be available to it) and reduces the stomach's capacity for food. The extent of compression is adjustable by addition or withdrawal of fluid from the balloon, for example, by employing a hypodermic syringe to remove fluid from the subcutaneously located adjusting port. The apparatus is believed to impart the same feeling of satiety and result in similar weight loss that patients have experienced who have had tumors or pancreatic pseudo-cysts that press on the stomach.

BRIEF DESCRIPTION OF THE DRAWINGS

FIG. 1 illustrates a partially cut away view of a patient after implantation and during outpatient adjustment of an implant apparatus according to the invention;

FIG. 2 illustrates a perspective view of an implant apparatus according to the invention;

FIG. 3 illustrates a view taken on line 3—3 of FIG. 1;

DETAILED DESCRIPTION OF A PREFERRED EMBODIMENT

Figure 4:
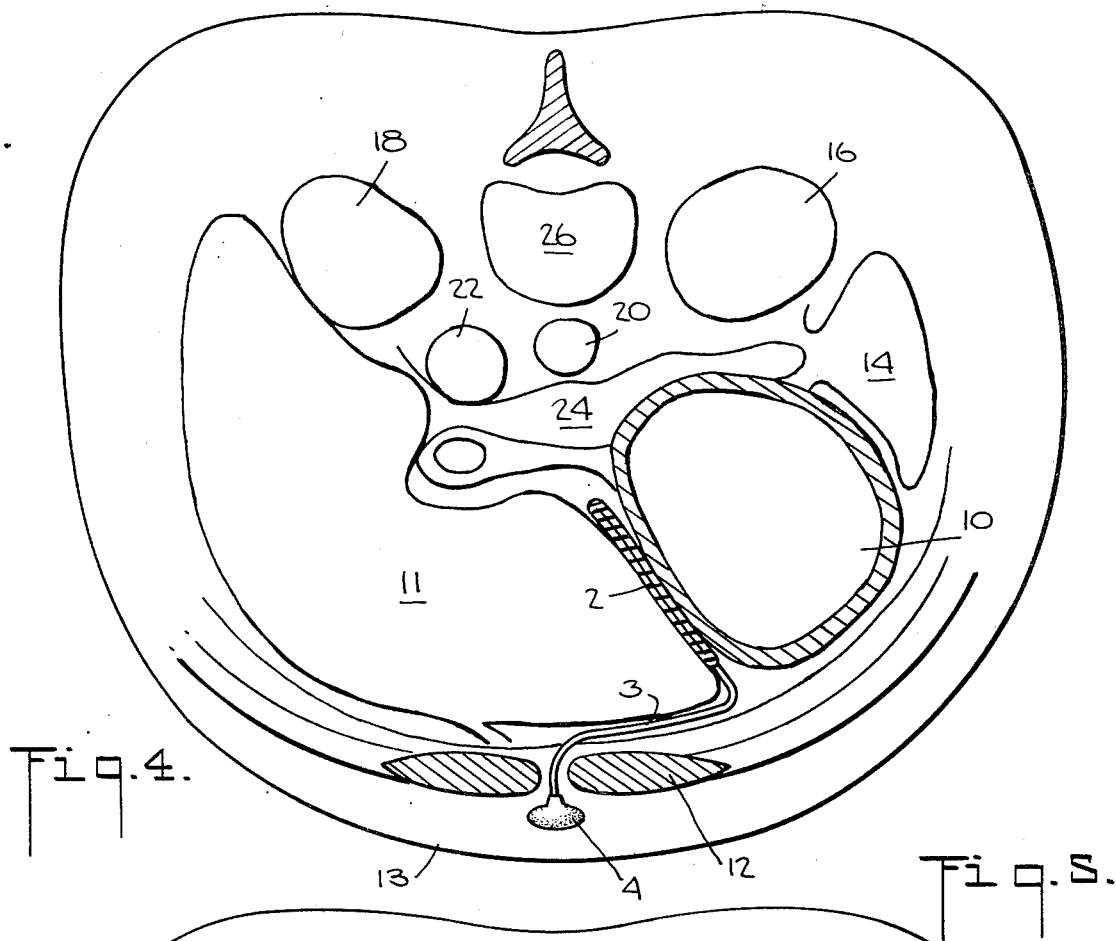
FIG. 4 illustrates a cross-sectional view of the human anatomy at the T-12 level after implantation and prior to inflation of an implant apparatus according to the invention.

Referring to FIG. 2, the implant apparatus is in the form of a gastric compression means 1 comprised of a gastric compression distensible means, such as a balloon 2, for example, of rubber, a filling tube 3 and an adjusting port 4.

The balloon 2 is distensible and is of a size adapted for implantation in an abdominal cavity of an obese patient 5 (FIG. 1). The dimensions of the balloon 2 are not critical but should be chosen so that a distension to a diameter of at least 20 centimeters (cm) would result if the balloon 2 were filled with fluid to an internal pressure of about 20 millimeters of mercury (mmHg) outside the patient in ambient air. These dimensions are suitable for an adult patient and may be scaled proportionally for younger patients. The balloon 2 may be made of any material that will not deteriorate in or interfere with the environment of the peritoneal cavity. Preferred materials are latex rubber or a medical grade silicone elastomer, such as Silastic, coated latex rubber. The balloon 2 has a single opening 5 which communicates with the filling tube 3 and may be formed integral with the balloon 2 or fastened by suitable adhesives 6 to form an airtight seal.

The filling tube 3 is in the form of an elongated neck fashioned of a flexible material suitable for use in the abdominal cavity such as plastic tubing and can be reinforced against twisting and collapse by a wire helix 7 or other reinforcing means. The helix 7 is preferably embedded in the wall of the filling tube 3 but may be attached in some other manner that permits the filling tube 3 to be easily cut during the implantation at any convenient point (to be described below) to a length appropriate for the patient without fraying or unraveling. The filling tube 3 is made of materials that will not resist lateral bending, which bending may otherwise cause discomfort to the patient, yet should be sufficiently stiff to permit insertion of an attachment nozzle (described below). Medical grade silicone elastomer is a preferred material. The diameter of the filling tube 3 should preferably be uniform at least at the positions where the tube 3 may be cut. The length of the filling tube 3 should be sufficient to reach from a patient's stomach to his anterior abdominal subcutaneous area.

Referring to FIGS. 2 and 3, the adjusting port 4 is formed from an elastomeric material adapted to be penetrated by a hypodermic needle 30 and to reseal upon removal of the needle. The adjusting port 4 is preferably a hollow spheroid having an interior space 8 communicating with an insert nozzle 9 extending outwardly from the surface of the port 4. The shape and diameter of the insert nozzle 9 should be adapted for insertion into and retention by the open end of the filling tube 3. The outside diameter of the adjusting port 4, i.e., the widest dimension, should be chosen large enough so as to be easily struck with a hypodermic needle after being located by feeling the port 4 as a lump under the patient's skin. The diameter should be chosen as small as convenient so as not to produce an unsightly lump after the patient has lost substantial weight. A reasonable diameter would be 3 centimeters (cm.). The surface of the port 4 is preferably a material such as medical grade silicone elastomer coated latex rubber which will reseal itself after removal of a hypodermic syringe. Tabs 33 allow the adjusting port to be secured to the fascia with sutures.

In use, the gastric compression means 1 is implanted using standard surgical techniques. The patient may be placed under general anaesthesia and an incision made in the midline of the abdomen between the xiphoid process and the umbilicus. As shown in FIG. 4, the distensible balloon 2, together with the attached filling tube 3 may be placed in the abdominal cavity in position to bear against the stomach 10 when inflated. The preferred position is shown in FIG. 4 as anterior to the stomach 10 and posterior to the left lobe of the liver 11.

The filling tube 3 is then brought out to a suitable location anterior to the fascia beneath the skin, in the fatty layer 13 at the patient's abdomen as shown in FIG. 4. The preferred path of the filling tube 3 is shown in FIG. 4 extending from the balloon 2 around the left lobe of the liver 11 anterior through the muscle wall 12 of the abdomen to a position beneath the skin and fatty layers 13 of the abdomen. The exact length of the tube 3 is not critical for this purpose and 40 cm. would be adequate for an adult patient.

For reference' sake, the other organs of the body located in proximity to the gastric compression apparatus shown in FIG. 4 are the spleen 14, left and right kidney 16 and 18, respectively, aorta 20, inferior vena cava 22, pancreas 24, and T-12 vertebral body 26.

Figure 5:
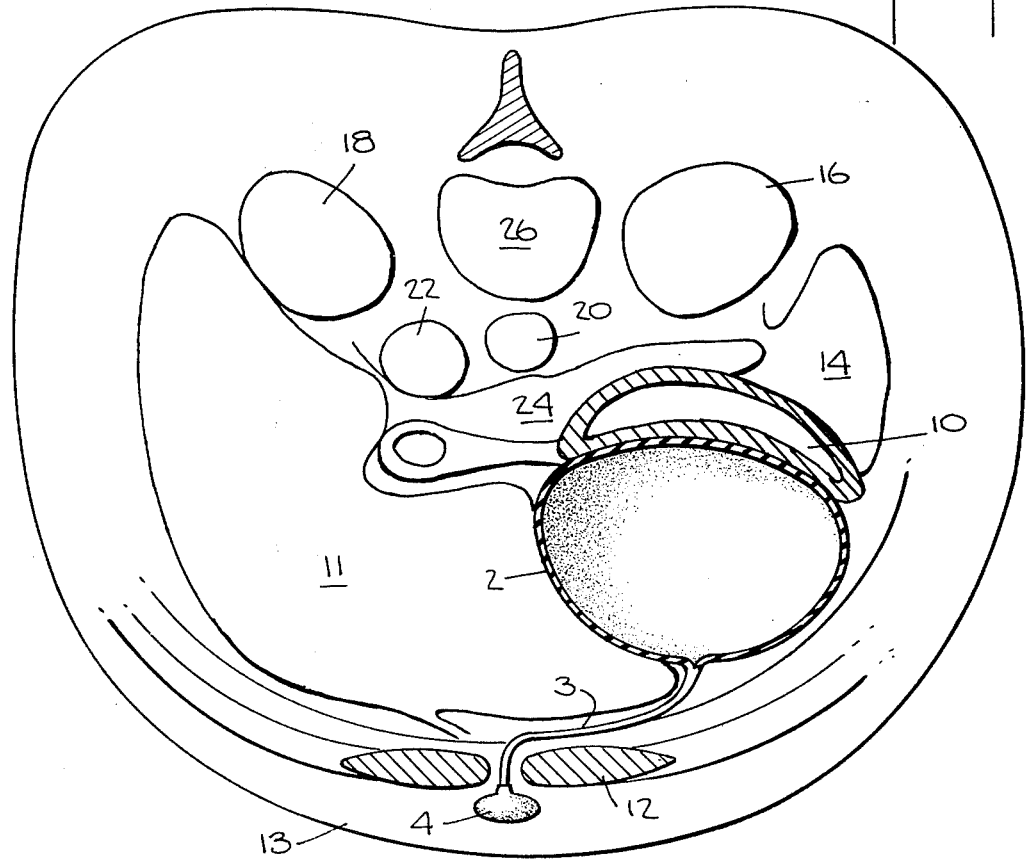
FIG. 5 illustrates a cross-sectional view of the human anatomy at the T-12 level after implantation and inflation of the implant apparatus of FIG. 4.

The open end of the filling tube 3 may then be cut to the appropriate length described above and the adjusting port 4 attached by inserting the insert nozzle 9 therein. The attachment may then be secured with non-absorbable sutures 28 (FIG. 3) and/or non-toxic adhesives. The adjusting port 4 is then located subcutaneously as shown in FIGS. 3, 4 and 5, and may be sutured to the fascia using non-absorbable sutures passed through suture tabs 33. The skin incision is closed using standard techniques.

Figure 6:
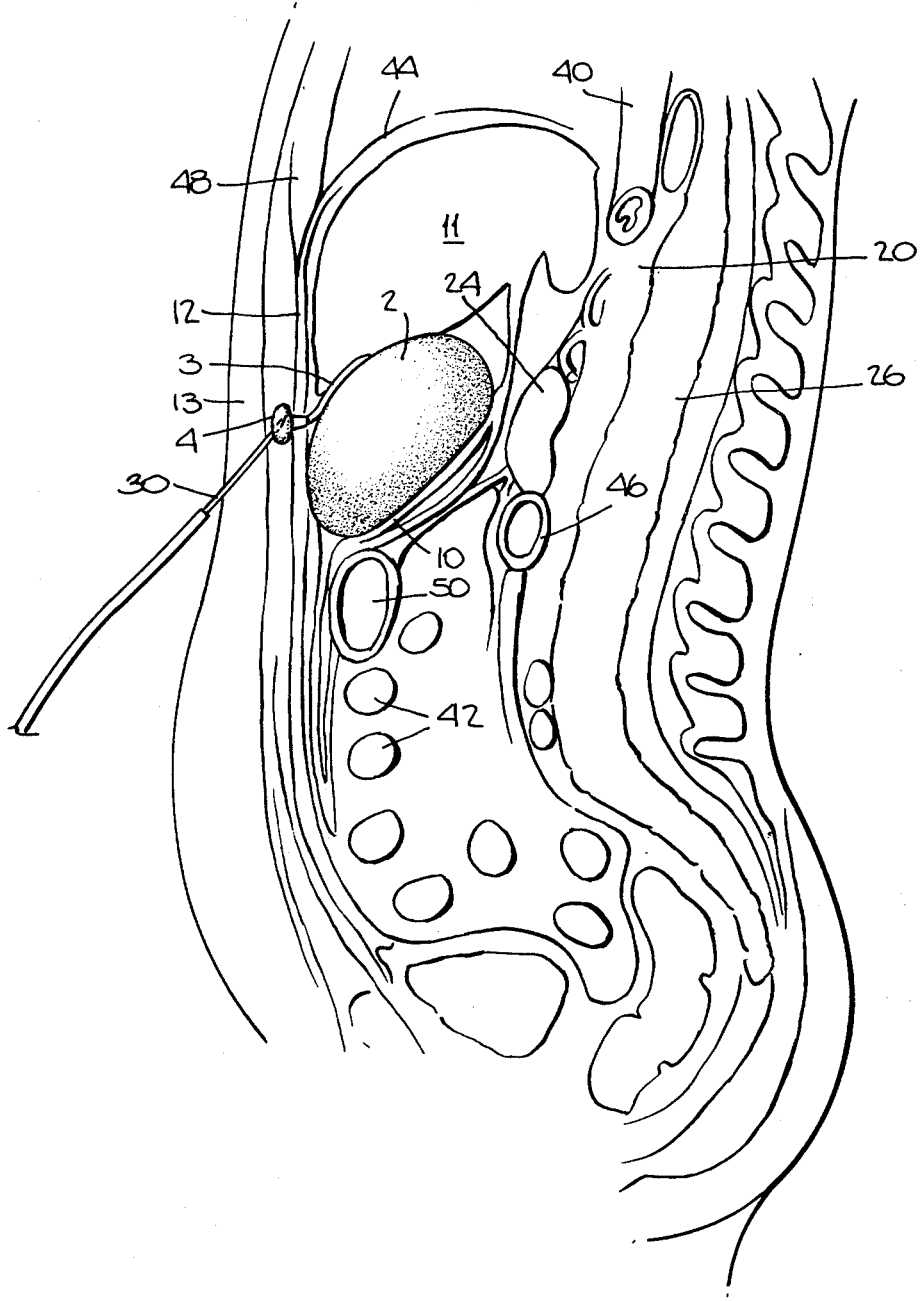
FIG. 6 illustrates a longitudinal cross-section view of the human anatomy after implantation and inflation of the implant apparatus.

After recovery from the abdominal surgery, the patient may be treated on an outpatient basis to increase or decrease the amount of inflation of the balloon 2 and thereby the amount of compression of the stomach 10. To induce a feeling of satiety and reduce the capacity of the stomach 10, a hypodermic needle 30 is introduced directly through the skin and fatty layers 13 into the adjusting port 4 as shown in FIGS. 1, 3 and 6. Fluid is then supplied to the needle 30 from a pressurized gas or liquid supply 32, preferably carbon dioxide gas at low pressure and body temperature. An appropriate pressure is about 20 mmHg. The carbon dioxide or other fluid then flows through the filling tube 3 to the balloon 2 which is then made to expand while compressing the stomach 10 as shown in FIGS. 5 and 6. FIG. 6 shows the location of the balloon in the patient after inflation and in connection with FIGS. 4 and 5 illustrates the placement of the gastric compression means. For reference' sake, the other organs of the body located in proximity to the gastric compression apparatus shown in FIG. 6 are the esophagus 40, small intestine 42, colon 50, diaphragm 44, duodenum (3rd part) 46, and sternum 48.

Carbon dioxide is used as the preferred fluid because there may be some inadvertent diffusion of the fluid into a patient's body cavity during use. As carbon dioxide has a relatively high diffusion rate into the blood stream, any tendency to collect in the patient is reduced. Further, experience with the use of carbon dioxide in laparoscopy indicates its safety. Of course, any other fluid or gas which can be safely utilized may be used.

I claim:

1. The method of treating extreme obesity in a patient comprising the steps of forming an incision in the abdomen of an obese patient;

surgically implanting an inflatable balloon in the abdominal cavity of the patient adjacent to the stomach, said balloon having a filling tube the distal end of which is sealingly attached in communication with a hollow spheroidal adjusting port of self-sealing elastomeric material;

suturing the adjusting port subcutaneously to the anterior wall of the fascia of the patient adjacent to the incision;

closing the incision over the adjusting port and subsequently locating the adjusting port by palpation; and inserting a hypodermic needle through the skin of the patient into the adjusting port and introducing a fluid under pressure into the port for passage through the filling tube into the balloon to expand the balloon to distend the upper abdomen and produce a sense of satiety, thereby reducing the patient's desire to ingest food, and to compress the stomach, thereby reducing its capacity.

* * * * *